(12) United States Patent
Coffin

(10) Patent No.: US 7,223,593 B2
(45) Date of Patent: May 29, 2007

(54) HERPES VIRUS STRAINS FOR GENE THERAPY

(75) Inventor: Robert Stuart Coffin, London (GB)

(73) Assignee: Biovex Limited, Oxford (GB)

( * ) Notice: Subject to any disclaimer, the term of this patent is extended or adjusted under 35 U.S.C. 154(b) by 339 days.

(21) Appl. No.: 10/181,697

(22) PCT Filed: Jan. 22, 2001

(86) PCT No.: PCT/GB01/00225

§ 371 (c)(1),
(2), (4) Date: Oct. 2, 2002

(87) PCT Pub. No.: WO01/53505

PCT Pub. Date: Jul. 26, 2001

(65) Prior Publication Data

US 2003/0091537 A1   May 15, 2003

(30) Foreign Application Priority Data

| Jan. 21, 2000 | (GB) | 0001475.3 |
| Feb. 8, 2000 | (GB) | 0002854.8 |
| Jan. 5, 2001 | (GB) | 0100288.0 |
| Jan. 6, 2001 | (GB) | 0100430.8 |

(51) Int. Cl.
*C12N 7/01* (2006.01)
*C12N 7/00* (2006.01)
*C12N 15/63* (2006.01)
*A61K 48/00* (2006.01)

(52) U.S. Cl. .......... 435/320.1; 435/235.1; 424/93.2

(58) Field of Classification Search ............ None
See application file for complete search history.

(56) References Cited

U.S. PATENT DOCUMENTS

| 5,328,688 A | 7/1994 | Roizman |
| 5,585,096 A | 12/1996 | Martuza et al. |
| 5,824,318 A | 10/1998 | Mohr et al. |
| 5,876,923 A | 3/1999 | Leopardi et al. |
| 6,428,968 B1 * | 8/2002 | Molnar-Kimber et al. . 435/7.23 |
| 6,641,817 B1 * | 11/2003 | Coffin et al. ............. 424/199.1 |
| 6,713,067 B2 * | 3/2004 | Coffin ..................... 424/199.1 |

FOREIGN PATENT DOCUMENTS

| GB | 2322130 | 8/1998 |
| WO | WO-92/13943 | 8/1992 |
| WO | WO-93/15749 | 8/1993 |
| WO | WO 93/19591 | 10/1993 |
| WO | WO-95/16779 | 6/1995 |
| WO | 96/16164 | 5/1996 |
| WO | WO-97/04804 | 2/1997 |
| WO | WO-97/20935 | 6/1997 |
| WO | WO-97/26904 | 7/1997 |
| WO | 98/04726 | 2/1998 |
| WO | WO 98/04726 | * 2/1998 |
| WO | WO-98/37905 | 9/1998 |
| WO | 98/42855 | 10/1998 |
| WO | 98/51809 | 11/1998 |
| WO | WO-99/07394 | 2/1999 |
| WO | WO 99/38955 | 8/1999 |
| WO | 00/08191 | 2/2000 |
| WO | WO-00/08051 | 2/2000 |
| WO | WO-00/40734 | 7/2000 |
| WO | WO 01 09361 | 2/2001 |
| WO | WO 01/46449 | 6/2001 |
| WO | WO 01/46450 | 6/2001 |
| WO | WO 01/53506 | 7/2001 |
| WO | WO 01/53507 | 7/2001 |

OTHER PUBLICATIONS

Rekabdar et al. (1999) Clin. Diag. Lab. Immunol., vol. 6 (6) 826-831.*
Andreansky et al. (1998) Gene Ther., vol. 5 (1), 121-130.*
Shi et al. (1999) Canc. Gene. Ther.,vol. 6(1) 81-88.*
Bronte et al. (1995) J. Immunol., vol. 154, 5282-5292.*
Irvine et al. (1996) J. Immunol., vol. 156, 238-245.*
Ace et al. "Construction and characterisation of a herpes simplex virus type 1 mutant unable to trasinduce immediate early gene expression" J. Virol. 63:2260-2269 (1989).
Chambers et al "Composition of genetically engineered herpes simplex viruses for the treatment of brain tumors in a SCID mouse model of human malignant glioma" Proc. Natl. Acad. Sci. USA 92:1411-1415 (1995).
Chou et al. "Mapping of herpes simplex virus-1 neurovirulence to γ34.5, a gene nonessential for growth in culture" Science 250:1262-1266 (1990).
DeLuca et al. "Isolation and characterisation of deletion mutants of herpes simplex virus type 1 in the gene encoding immediate-early regulatory protein ICP4" J. Virol. 56:558-570 (1985).
Gossen et al. "Transcriptional activation by tetracyclines in mammalian cells" Science 268:1766-1769 (1995).

(Continued)

Primary Examiner—Anne M. Wehbe
(74) Attorney, Agent, or Firm—Fulbright & Jaworski, LLP

(57) ABSTRACT

The present invention provides a herpes virus with improved oncolytic properties which comprises a gene encoding an immunomodulatory cytokine and which lacks a functional ICP34.5 gene and a functional ICP47 encoding gene.

4 Claims, 1 Drawing Sheet

OTHER PUBLICATIONS

Gossen & Bujard "Tight control of gene expression in mammalian cells by tetracyline-responsive promoters" Proc. Nat. Acad. Sci. USA 89:5547-5551 (1992).

Hill et al. "Herpes simplex virus turns off the TAP to evade host immunity" Nature 375:411-415 (1995).

Howard et al. "High efficiency gene transfer to the central nervous system of rodents and primates using herpes virus vectors lacking functional ICP27 and ICP34.5" Gene Therapy 5:1137-1147 (1998).

Hunter et al. "Attenuated replication-competent herpes simplex virus type 1 mutant G207: Safety evaluation of intracerebral injection in non-human primates" J. Virol. 73:6319-6326 (1999).

Krisky et al. "Deletion of multiple immediate-early genes from herpes simplex virus reduces cytotoxicity and permits long-term gene expression in neurons" Gene Therapy 5:1593-1603 (1998).

Maclean et al. "Herpes simplex virus type 1 deletion variants 1714 and 1716 pinpoint neurovirulence-related sequences in Glasgow strain 17+ between immediate early gene 1 and the "a" sequence" J. Gen. Virol. 72:631-639 (1991).

MacFarlane et al. "Hexamethylene bisacetamide stimulates herpes simplex virus immediate early gene expressions in the absence of trans-induction by Vmw65" J. Gen. Virology 73: 285-292 (1992).

Meignier et al. "In vivo behaviour of genetically engineered herpes simplex viruses R7017 and R7020: Construction and evaluation in rodents" J. Infect. Dis. 159:602-614 (1988).

Rice & Knipe "Genetic evidence for two distinct transactivation functions of the herpes simplex virus and protein ICP27" J. Virol. 64:1704-1715 (1990).

Samaniego et al. "Functional interactions between herpes simplex virus immediate-early proteins during infection: Gene expression as a consequence of ICP27 and different domains of ICP4" J. Virol. 69:5705-5715 (1995).

Samaniego et al. "Persistence and expression of the herpes simplex virus genome in the absence of immediate-early proteins" J. Virol. 72:3307-3320 (1998).

Shi et al. "Granulocyte-macrophage colony-stimulating factor (GM-CSF) secreted by cDNA-transfected tumor cells induces a more potent antitumor response than exogenous GM-CSF" Cancer Gene Therapy 6:81-88 (1999).

Smiley & Duncan "Truncation of the C-terminal acidic transcriptional activation domain of herpes simplex virus VP16 produces a phenotype similar to that of the in1814 linker insertion mutation" J. Virol. 71:6191-6193 (1997).

Smith et al. "Evidence that the herpes simplex virus immediate early protein ICP27 acts post-transcriptionally during infection to regulate gene expression" Virol. 186:74-86 (1992).

Thomas et al. "Herpes simplex virus latency associated transcript encodes a protein which greatly enhances virus growth, can compensate for deficiencies in immediate-early gene expression, and is likely to function during reactivation from virus latency" J. Virol. 73:6618-6625 (1999).

Thompson et al. "DNA sequence and RNA transcription through a site of recombination in a non-neurovirulent herpes simplex virus intertypic recombinant" Virus Genes 1:275-286 (1988).

Coukos et al; "Use of Carrier Cells to Deliver a Replication-selective Herpes Simplex Virus-1 Mutant for the Intraperitoneal Therapy of Epithelial Ovarian Cancer" Clinical Cancer Research vol. 5: 1523-1537 (1999).

Andreansky et al, "The Application of Genetically Engineered Herpes Simplex Viruses to the Treatment of Experimental Brain Tumors," Proc. Natl. Acad. Sci. vol. 93, pp. 11313-11318 (Oct. 1996).

Chou et al, "The γ134.5 Gene of Herpes Simplex Virus 1 Precludes Neuroblastoma Cells from Triggering Total Shutoff of Protein Synthesis Characteristic of Programmed cell Death in Neuronal Cells," Proc. Natl. Acad. Sci. vol. 89, pp. 3266-3270 (Apr. 1992).

Chou et al, "Differential response of Human Cells to Deletions and Stop Codons in the Y134.5 Gene of Herpes Simplex virus," Journal of Virology, pp. 8304-8311 (Dec. 1994).

Coukos et al, "Oncolytic Herpes Simplex Virus-1 Lacking ICP34.5 Induces p53-independent Death and Is Efficacious against Chemotherapy-resistant Ovarian Cancer," Clinical Cancer Research vol. 6, pp. 3342-3353 (Aug. 2000).

Ezzeddine et al, "Selective Killing of Glioma Cells in Culture and in Vivo by Retrovirus Transfer of the Herpes Simplex Virus Thymidine Kinase Gene," The New Biologist vol. 3, No. 6, pp. 608-614 (Jun. 1991).

Markert, James et al, "Reduction and Elimination of Encephalitis in an Experimental Glioma Therapy Model with attenuated Herpes Simplex Mutants that Retain Susceptibility to Acyclovir," Neurosurgery vol. 32 No. 4, pp. 597-603 (Apr. 1993).

Martuza et al, "Experimental Therapy of Human Glioma by Means of a Genetically Engineered Virus Mutant," Science vol. 252, pp. 854-856.

McKie et al, "Selective in Vitro Replication of Herpes Simplex Virus Type 1 (HSV-1) ICP34.5 Null Mutants in Primary Human CNS Tumours—Evaluation of a Potentially Effective Clinical Therapy," British Journal of Cancer vol. 74, pp. 745-752 (1996).

U.S. Appl. No. 10/181,692.

Krisky, D.M., et al.; Development of herpes simplex virus replication-defective multigene vectors for combination gene therapy applications; Gene Therapy 5:1517-1530, 1998.

Lachmann, Robin H., et al.; Gene transfer with herpes simplex vectors; Current Opinion in Molecular Therapeutics 1(5):622-632, 1999.

Liu, B.L., et al.; Research article—ICP34.5 deleted herpes simplex virus with enhanced oncolytic, immune stimulating , and anti-tumour properties; Gene Therapy 10:292-303, 2003.

Moriuchi, Shusuke, et al.; Enhanced Tumor Cell Killing in the Presence of Ganciclovir by Herpes Simplex Virus Type 1 Vector-directed Coexpression of Human Tumor Necrosis Factor-α and Herpes Simplex Virus Thymidine Kinase; Cancer Research 58:5731-5737, Dec. 15, 1998.

Mullen, John T., et al.; Viral Oncolysis; The Oncologist, 7:106-119, 2002.

Randazzo, Bruce P., et al.; Short Communications—Herpes Simplex 1716—an ICP 34.5 Mutant—Is Severely Replication Restricted in Human Skin Xenografts in Vivo Virology 223:392-395, 1996.

Speck, P. G., et al.; In vivo complementation studies of a glycoprotein H-deleted herpes simplex virus-based vector; Journal of General Virology 77:2563-2568, 1996.

Toda, Masahiro, et al.; In Situ Cancer Vaccination: An IL-12 Defective Vector/Replication-Competent Herpes Simplex Virus Combination Induces Local and Systemic Antitumor Activity; The Journal of Immunology 160:4457-4464, 1998.

Coukos, G., et al.; O-21: Producer cells enhance the oncolytic effect of a replication-competent ICP34.5-null herpes simplex virus-1 (HSV-1) strain in epithelial ovarian cancer; Conference Abstracts, Cancer Gene Therapy 5(6):57, 1998.

Toyoizumi, Takane, et al.; O-22: Combination therapy with herpes simplex virus type 1 ICP34.5 mutant (HSV-1716) and common chemotherapeutic agents for human non-small cell lung cancer (NSCLS); Conference Abstracts, Cancer Gene Therapy 5(6):57-58, 1998.

Andreansky, Samita, et al.; Evaluation of Genetically Engineered Herpes Simplex Viruses as Oncolytic Agent for Human Malignant Brain Tumors; Cancer Research 57:1502-1509; Apr. 15, 1997.

Mazda, O., et al.; Vector Systems/Gene Regulation; Conference Abstracts (O-20), Cancer Gene Therapy, 5(6):S7, 1998.

Dranoff, Glenn, et al.; Vaccination with irradiated tumor cells engineered to secrete murine granulocyte-macrophage colony-stimulating factor stimulates potent, specific, and long-lasting anti-tumor immunity; Proc. Natl. Acad. Sci. USA (Medical Sciences), 90:3539-3543, Apr. 1993.

Ejercito, Pilarica M., et al.; Characterization of Herpes Simplex Virus Strains Differing in their Effects on Social Behaviour of Infected Cells; J. gen. Virol. 2:357-364; Accepted Nov. 13, 1967.

Fulci, Giulia, et al.; Oncolytic Viruses for the Therapy of Brain Tumors and Other Solid Malignancies: A Review; Frontiers in Bioscience 8:e346-360, May 1, 2003.

Goldsmith, Kim, et al.; Infected Cell Protein (ICP)47 Enhances Herpes Simplex Virus Neurovirulence by Blocking the CD8+ T Cell Response; J. Exp. Med. 187(3):341-348, Feb. 2, 1998.

He, Bin, et al.; Suppression of the Phenotype of $_{\gamma 1}$34.5—Herpes Simplex Virus 1: Failure of Activated RNA-Dependent Protein Kinase To Shut Off Protein Synthesis Is Associated with a Deletion in the Domain of the α47 Gene; Journal of Virology, 71(8):6049-6054, Aug. 1997.

* cited by examiner

HERPES VIRUS STRAINS FOR GENE THERAPY

This application is the US national phase of international application PCT/GB01/00225 filed 22 Jan. 2001, which designated the US and was published in English.

FIELD OF THE INVENTION

The present invention relates to herpes virus strains with improved anti-tumour activity as compared to previously known strains.

BACKGROUND TO THE INVENTION

Viruses have been shown to have utility in a variety of applications in biotechnology and medicine on many occasions. Each is due to the unique ability of viruses to enter cells at high efficiency. This is followed in such applications by either virus gene expression and replication and/or expression of an inserted heterologous gene. Thus viruses can either deliver and express genes in cells (either viral or other genes) which may be useful in for example gene therapy or the development of vaccines, or they may be useful in selectively killing cells by lytic replication or the action of a delivered gene in for example cancer.

Herpes simplex virus (HSV) has been suggested to be of use for the oncolytic treatment of cancer. Here the virus must however be disabled such that it is no longer pathogenic, i.e. does not replicate in and kill non-tumor cells, but such that it can still enter and kill tumor cells. For the oncolytic treatment of cancer, which may also include the delivery of gene(s) enhancing the therapeutic effect, a number of mutations to HSV have been identified which still allow the virus to replicate in culture or in actively dividing cells in vivo (e.g. in tumors), but which prevent significant replication in normal tissue. Such mutations include disruption of the genes encoding ICP34.5, ICP6, and thymidine kinase. Of these, viruses with mutations to ICP34.5, or ICP34.5 together with mutation of e.g. ICP6 have so far shown the most favourable safety profile. Viruses deleted for only ICP34.5 have been shown to replicate in many tumor cell types in vitro and to selectively replicate in artificially induced brain tumors in mice while sparing surrounding tissue. Early stage clinical trials have also shown their safety in man.

However, while promise has been shown for various viruses including HSV for the oncolytic treatment of cancer, the majority of this work has used virus strains which do not carry a heterologous gene which may enhance the anti-tumor effect. We propose that the combined use of HSV with an inactivating mutation in the gene encoding ICP34.5 together with the delivery of the gene encoding an immunomodulatory protein such as granulocyte macrophage colony stimulating factor (GM-CSF) encoded in the disabled virus genome may have optimal immune stimulating properties against the tumor to be treated, particularly if functions in the virus which usually reduce immune responses to HSV infected cells have also been inactivated. For example the HSV ICP47 protein specifically inhibits antigen presentation in HSV infected cells (Hill et al 1995), and the product of the UL43 gene and the vhs protein reduce the immune-stimulating abilities of dendritic cells infected with HSV. ICP47 and/or dendritic cell-inactivating genes might therefore usefully be deleted from an oncolytic HSV mutant virus used for the treatment of cancer, particularly if immune effects are to be enhanced through the use of GM-CSF or other immunostimulatory cytokine or chemokine. GM-CSF has recently been shown to give an enhanced anti-tumor immune effect if expressed from within a tumor cell rather than administered systemically (Shi et al 1999). Thus in such use an oncolytic HSV mutant would be inoculated into a primary or secondary tumor where replication and oncolytic destruction of the tumor would occur. Immune responses would also be stimulated against the HSV infected cells, and also to tumor cells elsewhere which had spread from the primary tumor site.

SUMMARY OF THE INVENTION

The present invention provides viruses with improved capabilities for the lytic destruction of tumor cells in vivo. Here herpes simplex virus strains are constructed using a strain of HSV1 or HSV2 in which the genes encoding ICP34.5 and ICP47 have been inactivated such that a functional ICP34.5 or ICP47 protein cannot be expressed and which also carries a gene encoding an immunomodulatory protein. The virus may also be mutated for any additional gene(s) which may be involved in inhibiting the function of dendritic cells including the UL43 gene and/or the gene encoding vhs. The present invention therefore provides viruses capable of the oncolytic destruction of tumor cells and in which anti-tumor immune effects will have been maximised.

Accordingly the invention provides:

- a herpes virus which comprises a gene encoding an immunomodulatory protein and which lacks functional ICP34.5 and ICP47 encoding genes.
- a herpes virus of the invention for use in a method of treatment of the human or animal body by therapy.
- use of a virus of the invention in the manufacture of a medicament for the treatment of cancer.
- a pharmaceutical composition comprising as active ingredient a virus according to the invention and a pharmaceutically acceptable carrier or diluent.
- a method of treating a tumour in an individual in need thereof by administering to said individual an effective amount of a virus according to the invention.

DETAILED DESCRIPTION OF THE INVENTION

A. Viruses

Figure 1:
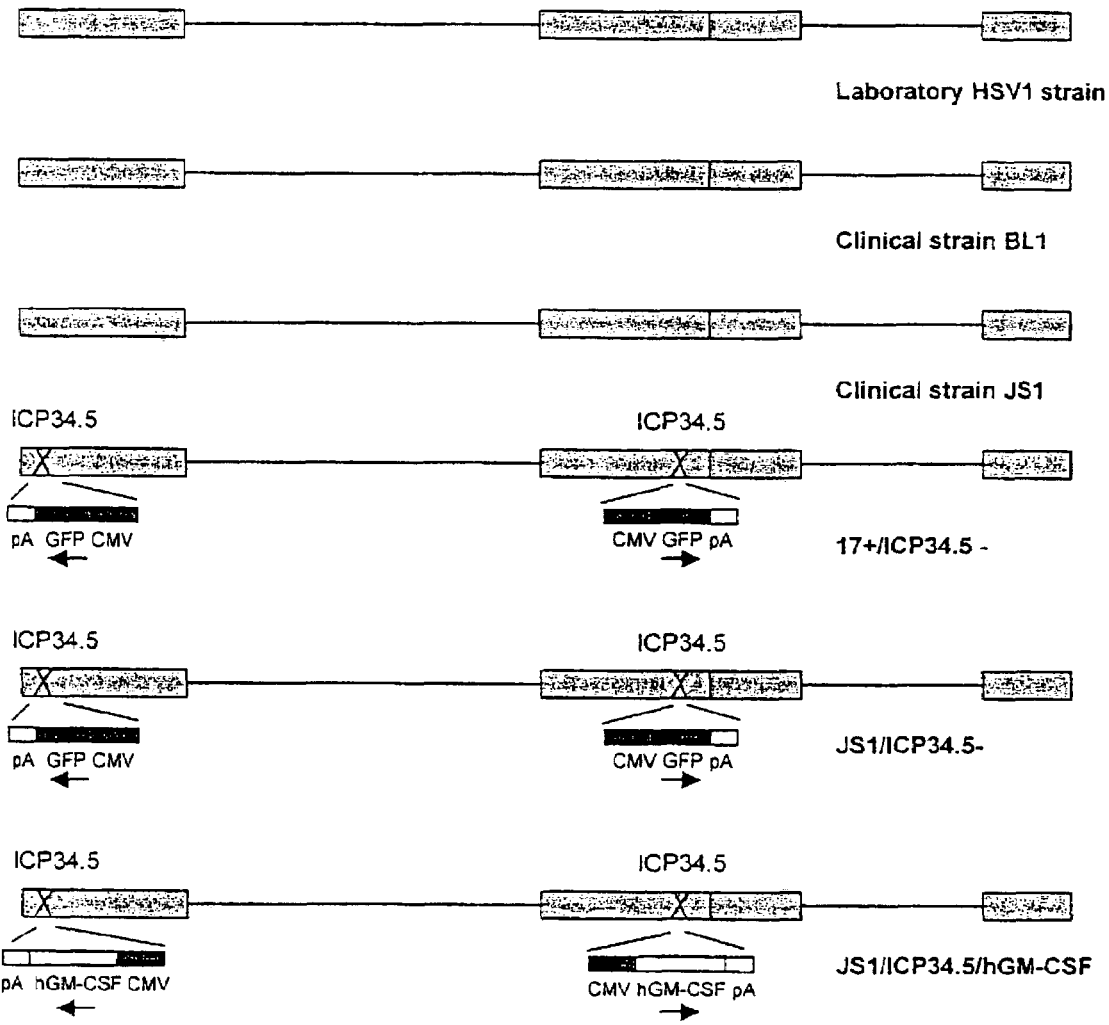
FIG. 1. Viruses
From top to bottom, diagrams show: laboratory HSV1 strain 17+, clinical HSV1 strain JS1, strain 17+/ICP34.5−, strain JS1/ICP34.5−, strain JS1/ICP34.5−/ICP47−/hG-MCSF, strain JS1/ICP34.5−/ICP47−/mGMCSF.

A herpes virus of the invention is capable of efficiently infecting target tumor cells and the genes encoding ICP34.5 and ICP47 are inactivated in the virus. Mutation of ICP34.5 allows selective oncolytic activity. Such mutations are described in Chou et al 1990 and Maclean et al 1991, although any mutation in which ICP34.5 is non-functional may be used. The genes encoding ICP6 and/or thyridine kinase may additionally be inactivated, as may other genes if such inactivation does significantly reduce the oncolytic effect, or if such deletion enhances oncolytic or other desirable properties of the virus. ICP47 usually functions to block antigen presentation in HSV-infected cells so its disruption leads to a virus that does not confer on infected tumour cells properties that might protect them from the host's immune system when infected with HSV. Viruses of the invention additionally encode an immunomodulatory protein, preferably GM-CSF, but may also encode other cytokines, chemokines such as RANTES, or other immunemodulatory proteins such as B7. 1. B7.2 or CD40L. Genes encoding immunomodulatory proteins may be included individually or in combination.

Viral regions altered for the purposes described above may be either eliminated (completely or partly), or made non-functional, or substituted by other sequences, in particular by a gene for an immunomodulatory protein such as GM-CSF.

The virus of the invention may be derived from a HSV1 or HSV2 strain, or from a derivative thereof, preferably HSV1. Derivatives include inter-type recombinants containing DNA from HSV1 and HSV2 strains. Such inter-type recombinants are described in the art, for example in Thompson et al, 1998 and Meignier et al, 1988. Derivatives preferably have at least 70% sequence homology to either the HSV1 or HSV2 genomes, more preferably at least 80%, even more preferably at least 90 or 95%. More preferably, a derivative has at least 70% sequence identity to either the HSV1 or HSV2 genome, more preferably at least 80% identity, even more preferably at least 90%, 95% or 98% identity.

For example the UWGCG Package provides the BESTFIT program which can be used to calculate homology (for example used on its default settings) (Devereux et al. (1984) *Nucleic Acids Research* 12, p387–395). The PILEUP and BLAST algorithms can be used to calculate homology or line up sequences (typically on their default settings), for example as described in Altschul (1993) J. Mol. Evol. 36:290–300; Altschul et al. (1990) J. Mol. Biol. 215:403–10.

Software for performing BLAST analyses is publicly available through the National Centre for Biotechnology Information's website. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al., 1990). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Nail. Acad. Sci. USA* 89: 10915–10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.*USA 90: 5873–5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

A derivative may have the sequence of a HSV1 or HSV2 genome modified by nucleotide substitutions, for example from 1, 2 or 3 to 10, 25, 50 or 100 substitutions. The HSV1 or HSV2 genome may alternatively or additionally be modified by one or more insertions and/or deletions and/or by an extension at either or both ends.

Virus strains of the invention may be "non-laboratory" strains. These can also be referred to as "clinical" strains. A person of skill in the art will readily be able to distinguish between a laboratory strain and a non-laboratory, or clinical, strain. Further guidance on the properties likely to be exhibited by virus strains is given below.

The key distinction between a laboratory and non-laboratory strain is that laboratory strains currently in common use have been maintained for long periods, many years in some cases, in culture. The culture of viruses such as HSV involves a technique known as serial passage. To grow and maintain viruses, suitable cells are infected with the virus, the virus replicates within the cell and the virus is then harvested; fresh cells are then re-infected, this process constitutes one cycle of serial passage. Each such cycle may take, for example, a few days in the case of HSV. As discussed above, such serial passaging may lead to changes in the properties of the virus strain, in that selection takes places for properties that favour growth in culture (e.g. rapid replication), as opposed to properties useful for practical applications, e.g. maintenance of the capacity to travel along axons in the case of HSV or to infect human cells.

Virus strains of the invention are may be non-laboratory strains in that they are derived from strains recently isolated from infected individuals. Strains of the invention are modified compared to the original clinical isolates, and may have spent a time in culture, but any time spent in culture will be comparatively short. Strains of the invention are prepared in such a manner as to retain substantially the desirable properties of the original clinical isolates from which they are derived.

A virus strain of the invention is derived from a parental virus strain if the parental virus strain is mutated to produce the virus. For example, a virus of the invention may be derived from the clinical isolate JSI. The parental strain of such a JSI-derived virus may be JSI or another HSV1 strain derived from JSI. Thus a virus of the invention may be a JSI virus comprising a gene encoding an immunomodulatory protein and which lacks a functional ICP34.5 encoding gene and a functional ICP47 encoding gene. In addition, such a virus may contain any other mutation as mentioned herein.

A virus of the invention is capable of efficiently infecting target human cancer cells. When such a virus is a non-laboratory or clinical strain it will have been recently isolated from an HSV infected individual and then screened for the desired ability of enhanced replication, infection or killing of tumour and/or other cells in vitro and/or in vivo in comparison to standard laboratory strains. Such viruses of the invention with improved properties as compared to laboratory virus strains are then engineered such that they lack functional ICP34.5 and ICP47 genes and encode a gene(s) for an immunomodulatory protein(s) such as GM-CSF under the control of a suitable promoter(s). Other genes encoding proteins which interfere with the function of dendritic cells such as UL43 and/or vhs may also be inactivated.

Preferably, a non-laboratory virus strain of the invention has undergone three years or less in culture since isolation of its unmodified clinical precursor strain from its host. More preferably, the strain has undergone one year or less in culture, for example nine months or less, six months or less, three months or less, or two months or less, one month or less, two weeks or less., or one week or less. By these definitions of time in culture, is meant time actually spent in culture. Thus, for example, it is a common practice to freeze virus strains in order to preserve them. Evidently, preserving by freezing or in an equivalent manner does not qualify as maintaining the strain in culture. Thus, time spent frozen or otherwise preserved is not included in the above definitions of time spent in culture. Time spent in culture is typically time actually spent undergoing serial passage, i.e. time during which selection for undesirable characteristics can occur.

Preferably, a non-laboratory virus strain has undergone 1,000 or less cycles or serial passage since isolation of its unmodified clinical precursor strain from its host. More preferably, it has undergone 500 or less, 100 or less, 90 or less, 80 or less, 70 or less, 60 or less, 50 or less, 40 or less, 30 or less, 20 or less, or 10 or less such cycles.

Preferably, a non-laboratory virus has a greater ability, as measured by standard statistical tests, than a reference laboratory strain with the equivalent modifications to perform certain functions useful in the application at hand. In the case of an oncolytic virus for tumour treatment, a non-laboratory virus strain of the invention will preferably have a greater ability than a reference laboratory strain with equivalent modifications to infect or replicate in tumour cells, to kill tumour cells or to spread between cells in tissue. More preferably, such greater ability is a statistically significantly greater ability. For example, according to the invention, a non-laboratory strain of the invention may have up to 1.1 fold, 1.2 fold, 1.5 fold, 2 fold, 5 fold, 10 fold, 20 fold, 50 fold, or 100 fold the capacity of the reference strain in respect of the property being tested.

Statistical analysis of the properties described herein may be carried out by standard tests, for example, t-tests, ANOVA, or Chi squared tests. Typically, statistical significance will be measured at a level of $p=0.05$ (5%), more preferably $p=0.01$ p, $p=0.001$, $p=0.0001$, $p=0.000001$.

Viruses of the invention infect and replicate in tumour cells, subsequently killing the tumour cells. Thus, such viruses are replication competent. Preferably, they are selectively replication competent in tumour cells. This means that either they replicate in tumour cells and not in non-tumour cells, or that they replicate more effectively in tumour cells than in non-tumour cells. Cells in which the virus is able to replicate are permissive cells. Measurement of selective replication competence can be carried out by the tests described herein for measurement of replication and tumour cell-killing capacity, and also analysed by the statistical techniques mentioned herein if desired.

A virus of the invention preferably has a greater ability than an unmodified parent strain to infect or replicate in a tumour cell, to kill tumour cells or to spread between cells in tissues. Preferably this ability is a statistically significant greater ability. For example, a virus according to the invention may have up to 1.1 fold, 1.2 fold, 1.5 fold, 2 fold, 5 fold, 10 fold, 20 fold, 50 fold or 100 fold the capacity of the unmodified parent strain in respect of the property being tested.

The properties of the virus strain in respect of tumour cells can be measured in any manner known in the art. For example, the capacity of a virus to infect a tumour cell can be quantified by measuring the dose of virus required to measure a given percentage of cells, for example 50% or 80% of cells. The capacity to replicate in a tumour cell can be measured by growth measurements such as those carried out in the Examples, e.g. by measuring virus growth in cells over a period of 6, 12, 24, 36, 48 or 72 hours or longer.

The ability of a virus to kill tumour cells can be roughly quantitated by eye or more exactly quantitated by counting the number of live cells that remain over time for a given time point and MOI for given cell type. For example, comparisons may be made over 24, 48 or 72 hours and using any known tumour cell type. In particular, HT29 colorectal adenocarcinoma, LNCaP.FGC prostate adenocarcinoma, MDA-MB-231 breast adenocarcinoma, SK-MEL-28 malignant melanoma or U-87 MG glioblastoma astrocytoma cells can be used. Any one of these cell types or any combination of these cell types can be used, as may other tumour cell types. It may be desirable to construct a standard panel of tumour cell types for this purpose. To count the number of live cells remaining at a given time point, the number of trypan blue-excluding cells (i.e. live cells) can be counted. Quantitation may also be carried out by fluorescence activated cell sorting (FACS) or MTT assay. Tumour cell-killing ability may also be measured in vivo, e.g. by measuring the reduction in tumour volume engendered by a particular virus.

In order to determine the properties of viruses of the invention, it will generally be desirable to use a standard laboratory reference strain for comparison. Any suitable standard laboratory reference strain may be used. In the case of HSV, it is preferred to use one or more of HSV1 strain 17+, HSV1 strain F or HSV1 strain KOS. The reference strain will typically have equivalent modifications to the strain of the invention being tested. Thus, the reference strain will typically have equivalent modifications gene deletions and, such as heterologous gene insertions. In the case of a virus of the invention, where the ICP34.5 and ICP47-encoding genes have been rendered non-functional, then they will also have been rendered nonfunctional in the reference strain. The modifications made to the reference strain may be identical to those made to the strain of the invention. By this, it is meant that the gene disruptions in the reference strain will be in exactly equivalent positions to those in the strain of the invention, e.g. deletions will be of the same size and in the same place. Similarly, in these embodiments, heterologous genes will be inserted in the same place, driven by the same promoter, etc. However, it is not essential that identical modifications be made. What is important is that the reference gene has functionally equivalent modifications, e.g. that the same genes are rendered nonfunctional and/or the same heterologous gene or genes is inserted.

B. Methods of Mutation

The various genes referred to may be rendered functionally inactive by several techniques well known in the art. For example, they may be rendered functionally inactive by deletion(s), substitution(s) or insertion(s), preferably by deletion. Deletions may remove one or more portions of the gene or the entire gene. For example, deletion of only one nucleotide may be made, resulting in a frame shift. However, preferably a larger deletion( ) is made, for example at least 25%, more preferably at least 50% of the total coding and non-coding sequence (or alternatively, in absolute terms, at least 10 nucleotides, more preferably at least 100 nucleotides, most preferably, at least 1000 nucleotides). It is particularly preferred to remove the entire gene and some of the flanking sequences. Where two or more copies of the gene are present in the viral genome it is preferred that both copies of the gene are rendered functionally inactive.

Mutations are made in the herpes viruses by homologous recombination methods well known to those skilled in the art. For example, HSV genomic DNA is transfected together with a vector, preferably a plasmid vector, comprising the mutated sequence flanked by homologous HSV sequences. The mutated sequence may comprise a deletion(s), insertion(s) or substitution(s), all of which may be constructed by routine techniques. Insertions may include selectable marker genes, for example lacZ or green fluorescent protein (GFP), for screening recombinant viruses, for example, β-galactosidase activity or fluorescence.

C. Heterologous Genes and Promoters

The viruses of the invention may be modified to carry a heterologous gene encoding an immunomodulatory protein. Preferably the immunomodulatory protein will enhance the anti-tumour activity of the virus. More preferably the protein is GM-CSF or another cytokine, a chemokine such as RANTES, or another immunomodulatory molecule such as B7.1, B7.2 or CD40L. Most preferably the immunomodulatory molecule is GM-CSF. The immunomodulatory gene may be any allelic variant of a wild-type gene, or it may be a mutant gene. The immunomodulatory gene will be derived from a mammal, preferably a rodent or primate, more preferably a human. The immunomodulatory gene is preferably operably linked to a control sequence permitting expression of said gene in a cell in vivo. Viruses of the invention may thus be used to deliver the immunomodulatory gene (or genes) to a cell in vivo where it will be expressed.

The immunomodulatory gene may be inserted into the viral genome by any suitable technique such as homologous recombination of HSV strains with, for example, plasmid vectors carrying the gene flanked by HSV sequences. The GM-CSF gene, or other immunomodulatory gene, may be introduced into a suitable plasmid vector comprising herpes viral sequences using cloning techniques well-known in the art. The gene may be inserted into the viral genome at any location provided that oncolytic properties are still retained. Immunomodulatory genes may be inserted at multiple sites within the virus genome. For example, from 2 to 5 genes may be inserted into the genome.

The transcribed sequence of the immunomodulatory gene is preferably operably linked to a control sequence permitting expression of the gene in a tumour cell. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence.

The control sequence comprises a promoter allowing expression of the immunomodulatory gene and a signal for termination of transcription. The promoter is selected from promoters which are functional in mammalian, preferably human tumour cells. The promoter may be derived from promoter sequences of eukaryotic genes. For example, the promoter may be derived from the genome of a cell in which expression of the heterologous gene is to occur, preferably a mammalian, preferably a human tumour cell. With respect to eukaryotic promoters, they may be promoters that function in a ubiquitous manner (such as promoters of β-actin, tubulin) or, alternatively, in a tumour-specific manner. They may also be promoters that respond to specific stimuli, for example promoters that bind steroid hormone receptors. Viral promoters may also be used, for example the Moloney murine leukaemia virus long terminal repeat (MMLV LTR) promoter or other retroviral promoters, the human or mouse cytomegalovirus (CMV) IE promoter, or promoters of herpes virus genes including those driving expression of the latency associated transcripts.

Expression cassettes and other suitable constructs comprising the immunomodulatory gene and control sequences can be made using routine cloning techniques known to persons skilled in the art (see, for example, Sambrook et al., 1989, Molecular Cloning—A laboratory manual; Cold Spring Harbor Press).

It may also be advantageous for the promoters to be inducible so that the levels of expression of the immunomodulatory gene(s) can be regulated during the life-time of the tumour cell. Inducible means that the levels of expression obtained using the promoter can be regulated. For example, a virus of the invention may further comprise a hererologous gene encoding the tet repressor/VP16 transcriptional activator fusion protein under the control of a strong promoter (e.g. the CMV IE promoter) and the immunomodulatory gene may be under the control of a promoter responsive to the tet repressor VP 16 transcriptional activator fusion protein previously reported (Gossen and Bujard, 1992, Gossen et al, 1995). Thus, in this example, expression of the immunomodulatory gene would depend on the presence or absence of tetracycline.

Multiple heterologous genes can be accommodated in the herpes virus genome. Therefore, a virus of the invention may comprise two or more immunomodulatory genes, for example from 2 to 3, 4 or 5 immunomodulatory genes. More than one gene and associated control sequences could be introduced into a particular HSV strain either at a single site or at multiple sites in the virus genome. Alternatively pairs of promoters (the same or different promoters) facing in opposite orientations away from each other, each driving the expression of an immunomodulatory gene may be used.

D. Therapeutic Uses

Viruses of the invention may be used in methods of cancer therapy of the human or animal body. In particular, viruses of the invention may be used in the oncolytic treatment of cancer, either with or without additional pro-drug therapy or stimulation of an anti-tumour immune response. Viruses of the invention may be used in the therapeutic treatment of any solid tumour in a mammal, preferably in a human. For example viruses of the invention may be administered to a subject with prostate, breast, lung, liver, endometrial, bladder, colon or cervical carcinoma; adenocarcinoma; melanoma; lymphoma; glioma; or sarcomas such as soft tissue and bone sarcomas.

E. Administration

The viruses of the invention may be used in a patient, preferably a human patient, in need of treatment. A patient in need of treatment is an individual suffering from cancer, preferably an individual with a solid tumour. The aim of therapeutic treatment is to improve the condition of a patient. Typically therapeutic treatment using a virus of the invention allieviates the symptoms of the cancer. A method of treatment of cancer according to the invention comprises administering a therapeutically effective amount of a virus of the invention to a patient suffering from cancer. Administration of an oncolytic virus of the invention to an individual suffering from a tumour will typically kill the cells of the tumour thus decreasing the size of the tumour and/or preventing spread of malignant cells from the tumour.

One method of administering therapy involves combining the virus with a pharmaceutically acceptable carrier or diluent to produce a pharmaceutical composition. Suitable carriers and diluents include isotonic saline solutions, for example phosphate-buffered saline.

Therapeutic treatment may be carried out following direct injection of the virus composition into target tissue which may be the tumour or a blood vessel supplying the tumour. The amount of virus administered is in the case of HSV in the range of from $10^4$ to $10^{10}$ pfu, preferably from $10^5$ to $10^8$ pfu, more preferably about $10^6$ to $10^8$ pfu. Typically up to 500 µl, typically from 1 to 200 µl preferably from 1 to 10 µl of a pharmaceutical composition consisting essentially of the virus and a pharmaceutically acceptable suitable carrier or diluent would be used for injection. However for some oncolytic therapy applications larger volumes up to 10 ml may also be used, depending on the tumour and the inoculation site.

The routes of administration and dosages described are intended only as a guide since a skilled practitioner will be able to determine readily the optimum route of administration and dosage. The dosage may be determined according to various parameters, especially according to the location of the tumour, the size of the tumour, the age, weight and condition of the patient to be treated and the route of administration. Preferably the virus is administered by direct injection into the tumour. The virus may also be administered systemically or by injection into a blood vessel supplying the tumour. The optimum route of administration will depend on the location and size of the tumour.

The following Examples illustrates the invention.

Herpes simplex type-1 virus (HSV1) in which the neurovirulence factor ICP34.5 is inactivated has previously been shown to direct tumour specific cell lysis in tumour models both in vitro and in vivo. Such viruses have also been shown to be safe in Phase I clinical trials by direct intracerebral injection in late stage glioma patients.

Previous work has used serially passaged laboratory isolates of HSV1 (viruses derived from HSV1 strain 17+ or HSV1 strain F) which might be anticipated to be attenuated in their lytic capability in human tumour cells as compared to more recent clinical isolates.

In work aimed at producing ICP34.5 deleted HSV with enhanced oncolytic and anti-tumour potential, we have deleted ICP47 and ICP34.5 from HSV1 strain JS1 and have inserted the immunomodulatory gene for GM-CSF.

Virus Construction (see FIG. 1)

The viruses used were either based on HSV1 strain 17+ (a standard laboratory strain) or a clinical isolate derived from cold sores from a frequent re-activator of HSV1. This clinical, or "non-laboratory", strain is named JS1. ICP34.5 was completely deleted from strain 17+ and JS 1 together with the insertion of a CMV-GFP cassette. JS1 was then also further engineered by the insertion of human GM-CSF (hGM-CSF) or mouse GM-CSF (mGM-CSF) so as to replace the ICP34.5 gene and by the deletion of ICP47. The derivatives of JS1 discussed herein are also non-laboratory strains, i.e. modified non-laboratory strains of the invention.

Lytic Capabilities of Viruses

Lytic (cell killing) capabilities were enhanced with the JS1-derived non-laboratory strains derived virus in all tumour cell lines tested as compared with the 17+ derived strains. More particularly, the JS1/34.5– virus, i.e. JS1 with ICP34.5 removed by deletion, showed enhanced lytic capabilities in HT29 colorectal adenocarcinoma, LNCaP.FGC prostate adenocarcinoma, MDA-MB-231 breast adenocarcinoma, SK-MEL-28 malignant melanoma and U-87 MG glioblastoma astrocytoma cells.

Thus, to provide increased oncolytic activity, the use of recent clinical virus strains is likely to enhance the anti-tumour capabilities of such viruses when used in human patients for cancer treatment.

Further Enhanced Anti-Tumour Activity

Further enhanced activity may also be anticipated if these viruses are then used to deliver genes with anti-tumour activity. Such genes include those encoding pro-drug activators or immunostimulatory proteins.

An ICP34.5 deleted clinical isolated of HSV1 which expresses human or mouse GM-CSF was produced from JS1. GM-CSF is a potent immune stimulator. These virus are designed to enhance anti-tumour immune responses following intra-tumoral injection. These viruses were demonstrated to express human or mouse GM-CSF using ELISA assay kits (Biotrak, Amersham) when the viruses are produced in BHK cells in culture. Individual wells of a six well plate produced 0.56 or 0.54 microgrammes of human or mouse GM-CSF respectively 24 hrs after infection of confluent BHK cells at MOI=0.5.

Deposit Information

HSV1 strain JS1 has been deposited at the European Collection of Cell Cultures (ECACC), CAMR, Sailsbury, Wiltshire SP4 PJG, United Kingdom, on 2 Jan. 2001 under accession number 01010209.

REFERENCES

Hill et al. 1995, Nature 375; 411–415
Shi et al. 1999, Cancer-Gene-Ther 6: 81–88
Chou et al. 1990, Science 250: 1262–1266
Maclean et al. 1991, J. Gen. Virol. 72: 631–639
Gossen M & Bujard H, 1992, PNAS 89: 5547–5551
Gossen M et al. 1995, Science 268: 1766–1769
Thompson et al. 1998, Virus Genes 1(3); 275–286
Meignier et al. 1988, Infect. Dis. 159; 602–614

The invention claimed is:

1. A herpes simplex virus which:
   (i) comprises a gene encoding an immunostimulatory protein;
   (ii) lacks a functional ICP34.5 encoding gene and a functional ICP47 encoding gene;
   (iii) is replication competent in tumor cells; and
   (iv) is derived from HSV1 JS1 as deposited at the European collection of cell cultures (ECAAC) under accession number 01010209.

2. A virus according to claim 1, wherein said immunostimulatory protein is GM-CSF.

3. A pharmaceutical composition comprising as active ingredient a virus according to claim 1 and a pharmaceutically acceptable carrier or diluent.

4. HSV1 strain JS1 as deposited at the European Collection of Cell Cultures (ECACC) under accession number 01010209, or an HSV1 strain derived therefrom.

* * * * *